(12) United States Patent
Majima et al.

(10) Patent No.: US 9,523,643 B2
(45) Date of Patent: Dec. 20, 2016

(54) PROTEIN CONCENTRATION ASSAY METHOD INCLUDING PH MEASUREMENT

(71) Applicant: ARKRAY, Inc., Kyoto (JP)

(72) Inventors: Satoshi Majima, Kyoto (JP); Shinya Nakajima, Kyoto (JP)

(73) Assignee: ARKRAY, INC., Kyoto (JP)

(*) Notice: Subject to any disclaimer, the term of this patent is extended or adjusted under 35 U.S.C. 154(b) by 1058 days.

(21) Appl. No.: 13/652,292

(22) Filed: Oct. 15, 2012

(65) Prior Publication Data

US 2013/0102082 A1 Apr. 25, 2013

(30) Foreign Application Priority Data

Oct. 17, 2011 (JP) ................. 2011-228319
Oct. 1, 2012 (JP) ................. 2012-219077

(51) Int. Cl.
*G01N 21/80* (2006.01)
*G01N 33/68* (2006.01)
*G01N 33/52* (2006.01)

(52) U.S. Cl.
CPC .............. *G01N 21/80* (2013.01); *G01N 33/52* (2013.01); *G01N 33/6839* (2013.01)

(58) Field of Classification Search
None
See application file for complete search history.

(56) References Cited

U.S. PATENT DOCUMENTS

| 3,485,587 A | | 12/1969 | Keston | |
|---|---|---|---|---|
| 5,077,222 A | * | 12/1991 | Lau | ........... G01N 33/523 422/424 |
| 5,183,742 A | * | 2/1993 | Omoto | ........... C12Q 1/28 422/421 |

(Continued)

FOREIGN PATENT DOCUMENTS

CN 2651751 Y 10/2004
EP 0545128 A1 6/1993

(Continued)

OTHER PUBLICATIONS

Wills, M.R. et al. "The reliability of the Albustix test for proteinuria," J. Clin. Pathol. Sep. 1963; 16(5): 487.*

(Continued)

*Primary Examiner* — Yelena G Gakh
*Assistant Examiner* — Michelle Adams
(74) *Attorney, Agent, or Firm* — Knobbe, Martens Olson & Bear LLP (57) ABSTRACT

Provided is a protein concentration assay method that uses a protein indicating reagent and that enables highly accurate assay. The protein concentration assay method includes: optically analyzing a color exhibited after a sample to be assayed and a protein indicating reagent are brought into contact with each other; measuring pH of the sample to be assayed; and assaying a concentration of protein in the sample based on the result of the optical analysis, the measured value of pH, and data for protein concentration assay, wherein the protein indicating reagent is a protein (Continued)

indicating reagent whose color varies with pH and a concentration of protein, and the data for protein concentration assay include information indicating a way to assay the result of the optical analysis corresponding to the measured value of pH.

9 Claims, 6 Drawing Sheets

(56) References Cited

U.S. PATENT DOCUMENTS

| | | | |
|---|---|---|---|
| 5,326,707 | A | 7/1994 | Franke et al. |
| 5,593,895 | A | 1/1997 | Cahill et al. |
| 6,815,210 | B1 * | 11/2004 | Profitt ............... G01N 33/6839 422/424 |
| 2006/0140818 | A1 | 6/2006 | Sakamoto et al. |
| 2011/0224516 | A1 * | 9/2011 | Romey ............. A61B 5/14532 600/317 |

FOREIGN PATENT DOCUMENTS

| | | |
|---|---|---|
| EP | 1715347 A1 | 10/2006 |
| JP | 5-249122 A | 9/1993 |
| JP | 09-145711 A | 6/1997 |
| JP | 2000-321270 A | 11/2000 |
| WO | 02/04658 A1 | 1/2002 |
| WO | 2005/038456 A1 | 4/2005 |

OTHER PUBLICATIONS

Yasuda, G. et al, A new protein titrator tape for self-assessment by outpatients with proteinuria, Nihon Jinzo Gakkai Shi, Sep. 1995, pp. 511-517, vol. 37, No. 9, Japan.

Extended European Search Report for Application No. 12188737.6 dated Mar. 14, 2013.

* cited by examiner

PROTEIN CONCENTRATION ASSAY METHOD INCLUDING PH MEASUREMENT

TECHNICAL FIELD

The present disclosure relates to a protein concentration assay method, an analysis tool, and an analyzer.

BACKGROUND ART

A method for conveniently measuring a protein concentration in an aqueous liquid sample containing a protein, such as urine (JP5 (1993)-249122A), is known. The method uses a pH indicating dye that exhibits a color transition when the dye reacts with a protein, thereby forming a protein indicating reagent. Such a protein indicating reagent has a color that also varies with pH, but changes in the color may correlate with protein concentrations when the pH is kept constant. Examples of such a protein indicating reagent include tetrabromophenol blue (TBPB) and tetrachlorophenol-3,4,5,6-tetrabromosulfophthalein. Since a change in pH causes the color of the protein indicating reagent to change, independently from the concentration of protein, the use of such a protein indicating reagent requires the use of a buffer in combination so as to keep pH constant.
(JP5 (1993)-249122A, U.S. Pat. No. 3,485,587).

SUMMARY

However, in the case where a sample such as urine has a pH different from a predetermined pH over a buffer effect, a protein concentration measured by the protein indicating reagent alone is different from the actual protein concentration in the sample, which problematically may lead to a false positive or a false in determination of a disease or the like.

Thus, the present disclosure in one aspect provides a protein concentration assay method for assaying a concentration of protein in a sample using the protein indicating reagent, yielding a protein concentration assay method that is capable of performing with high accuracy.

The present disclosure in one aspect relates to a protein concentration assay method for assaying a concentration of protein in a sample, and the method includes: optically analyzing a color exhibited after the sample and a protein indicating reagent are brought into contact with each other; measuring pH of the sample; and assaying a concentration of protein in the sample based on the result of the optical analysis, the measured value of pH, and data for protein concentration assay, wherein the protein indicating reagent is a protein indicating reagent whose color varies with pH and a concentration of protein, and the data for protein concentration assay include information indicating a way to assay the result of the optical analysis corresponding to the measured value of pH.

The present disclosure in another aspect relates to an analysis tool having a plurality of reagent layers formed on a substrate, wherein the plurality of reagent layers include a reagent layer A, containing a protein indicating reagent whose color varies with pH and a protein concentration, and a reagent layer B, containing a pH indicating reagent, and the reagent layer A and the reagent layer B contain a buffer so as to have the same buffer condition.

The present disclosure in still another aspect relates to an analyzer that includes: a measurement section that optically analyzes a color exhibited after the sample and a protein indicating reagent are brought into contact with each other; a measurement section that measures pH of the sample; an assay section that assays a concentration of protein in the sample based on the result of the optical analysis, the measured value of pH, and data for protein concentration assay; and an output section that outputs data after assay, wherein the protein indicating reagent is a protein indicating reagent whose color varies with pH and a concentration of protein, and the data for protein concentration assay include information indicating a way to assay the result of the optical analysis corresponding to the measured value of pH.

According to the present disclosure, in one or a plurality of embodiments, the accuracy of the protein concentration assay using a protein indicating reagent can be improved, and further in one or a plurality of embodiments, the occurrence of a false positive or a false negative can be suppressed.

DETAILED DESCRIPTION

Protein contained in urine is generally referred to as urine protein. The concentration of urine protein is, on average, about 10 to 20 mg/dL in the case of a normal individual, but with any abnormality in the kidney, the ureter, the bladder, or the like, the concentration of urine protein varies (increases), which is well known. Therefore, the measurement of the urine protein is important from the viewpoint that it is an indicator for diseases in the foregoing organs.

A protein indicating reagent used as an analysis tool for urine protein measurement is generally a reagent that can also be used as a pH indicating reagent and is very easily influenced by pH. Therefore, conventionally, such a protein indicating reagent is often used in combination with a buffer for keeping pH at a constant level. Depending on a sample to be measured, however, pH may vary, beyond the buffer effect. In the case where a sample having a pH different from an assumed pH is measured with the protein indicating reagent alone, the measurement lacks accuracy and can lead to a false positive or a false negative in the determination of presence/absence of a disease.

The present disclosure is based on the finding that, by using the pH of a sample to be assayed that is measured upon contact between the protein indicating reagent and the sample and appropriately correcting the result of optical analysis with use of the protein indicating reagent the accuracy of protein concentration assay can be improved, thereby further suppressing the occurrence of a false positive or false negative result.

In other words, in one aspect, the present disclosure relates to a protein concentration assay method for assaying a concentration of protein in a sample (hereinafter also referred to as the "assay method of the present disclosure"), and the method includes: optically analyzing a color exhibited after the sample and a protein indicating reagent are brought into contact with each other; measuring pH of the sample; and assaying a concentration of protein in the sample based on the result of the optical analysis, the measured value of pH, and data for protein concentration assay, wherein the protein indicating reagent is a protein indicating reagent whose color varies with pH and a concentration of protein, and the data for protein concentration assay include information indicating a way to assay the result of the optical analysis corresponding to the measured value of pH.

[Protein Indicating Reagent]

The "protein indicating reagent" as described herein refers to a reagent whose color varies with pH and protein concentration. The protein indicating reagent, in one or a plurality of embodiments, exhibits a color transition upon contact with protein in a solution and enables the detection of the presence of the protein in the solution and/or the measurement of concentration thereof. As the protein indicating reagent, many protein indicating reagents whose colors vary with pH are known. Also, in the present specification, the "protein indicating reagent" refers to one whose color varies with pH unless otherwise provided. As the protein indicating reagent, one that is conventionally known and/or to be developed in future can be used. For example, one disclosed in Patent Document 1 or the like can be used. Specific examples of the protein indicating reagent include octahalosulfophthalein-type dyes, octahalophenolphthalein-type dyes, and combinations of these. More specifically, examples of the protein indicating reagent include those selected from the group consisting of tetrabromophenol blue, tetrachlorophenol blue, 3',3",5,5"-tetraiode-3,4,5,6-tetrabromophenolsulfophthalein, 3,3"-diiode-5,5",3,4,5,6,-hexabromophenolsulfophthalein, methyl yellow (4-dimethylaminoazobenzen), and combinations of the same. Among these, tetrabromophenol blue is preferred, from the viewpoint of sensitivity and/or accuracy.

In the present disclosure, "bringing a sample and a protein indicating reagent into contact with each other" encompasses, for example, mixing a liquid sample and a solution of the protein indicating reagent, dipping a test piece (strip) having a reagent pad (reagent layer) that contains the protein indicating reagent in a dry state into a liquid sample, and the like. The form of the contact, however, is not limited to these, and it may be any form that has been known conventionally and/or is to be developed in future.

"Optical assay" as described herein is not limited particularly, and examples of the same include spectroscopic analysis that involves obtaining information relating to an object from transmitted light or scattered light from the object by using a spectroscope or the like. As a result of the optical analysis, for example, an absorbance, a transmittance, a reflectance, or the like of the object at a desired wavelength is obtained. An exemplary optical analysis is detecting transmitted light or scattered light of a protein indicating reagent or a pH indicating reagent that has been brought into contact with a sample and calculating a value indicative of an optical characteristic, such as an absorbance, a transmittance, or a reflectance, of the protein indicating reagent or the pH indicating reagent, from the detected light. It should be noted that the form of the optical analysis is not limited to these. Measurement using another optical method and/or a spectroscopic method is also included in the optical analysis.

In the case where the contact is provided by, for example, mixing of a liquid sample and the protein indicating reagent solution, "optically analyzing a color exhibited after the sample and the protein indicating reagent are brought into contact with each other" as described herein refers to optical analysis about the mixed solution. In the case where the contact is provided by immersing a reagent pad (reagent layer) containing the protein indicating reagent in a dry state into a liquid sample, the foregoing phrase refers to optical analysis about the reagent pad after the immersion. However, the optical analysis mentioned above may not be limited to those in such forms and may be in a conventionally known form and/or in a form to be developed in future. The "exhibited color" as described herein may include a color produced from a colorless state, and a color produced as a result of transition from another color.

The "sample" as described herein refers to an object that can contain protein and whose protein concentration is assayed by the assaying method of the present disclosure, and is also referred to as a "sample to be assayed" hereinafter. The sample to be assayed in the assaying method of the present disclosure is preferably a liquid, more preferably an aqueous liquid, from the viewpoint of improving the accuracy of the protein concentration assay with use of the protein indicating reagent. The protein as an object to be assayed is preferably dissolved in the liquid from the same viewpoint.

In the assay method of the present disclosure, the protein indicating reagent to be brought into contact with the sample to be assayed is generally 0.01 mg to 1 mg with respect to 1 mL of the sample to be assayed, and is preferably 0.02 mg to 0.5 mg with respect to 1 mL of the sample to be assayed, from the viewpoint of improving the accuracy of the protein concentration assay with use of the protein indicating reagent, and the viewpoint of economic efficiency.

[Buffer]

In the method for measuring a concentration of protein with use of the protein indicating reagent, usually a buffer is often used when the protein indicating reagent is mixed with the sample to be assayed, so as to keep pH constant. When the protein indicating reagent and the sample to be assayed are brought into contact with each other in the assaying method of the present disclosure as well, a buffer may be used. A buffer identical to those which have been used conventionally can be used, and any one may be selected appropriately according to the level of pH to be maintained. Examples of the buffer include citric acid, fumaric acid, tartaric acid, glycine, and malic acid. Among these, malic acid is preferred from the viewpoint of improving the accuracy of the protein concentration assay with use of the protein indicating reagent. The used amount of the buffer is usually 0.01 mg to 1 mg with respect to 1 mL of the sample to be assayed, and preferably 0.02 mg to 0.5 mg with respect to 1 mL of the sample to be assayed, from the viewpoint of improving the accuracy of the protein concentration assay with use of the protein indicating reagent and the viewpoint of economic efficiency. It should be noted that the measurement of pH of the sample to be assayed is preferably carried out under the same buffer conditions as those when the protein indicating reagent and the sample to be assayed are brought into contact, from the viewpoint of improving the accuracy of the protein concentration assay with use of the protein indicating reagent, as will be described later.

[Measurement of pH]

The assay method of the present disclosure includes measuring pH of the sample to be assayed. The method for measuring pH of the sample to be assayed is not limited particularly, and any known method can be used. For example, the method may be a method using a pH indicating reagent, or alternatively, a method using a pH meter. The measurement of pH is preferably carried out under the same buffer conditions as those when the protein indicating reagent and the sample to be assayed are brought into contact, from the viewpoint of improving the accuracy of the protein concentration assay with use of the protein indicating reagent. In the case where a buffer is added when the protein indicating reagent and the sample to be added are brought into contact, for example, the buffer is preferably added to the sample to be assayed upon the measurement of pH, so that the buffer has the same concentration. The pH described herein refers to pH at 25° C. unless otherwise provided.

[pH Indicating Reagent]

In the case where pH of a sample to be assayed is determined with use of a pH indicating reagent, the pH indicating reagent is preferably a pH indicating agent not prone to being influenced by the concentration of protein in the solution, from the viewpoint of improving the accuracy of the protein concentration assay with use of the protein indicating reagent. As such, a pH indicating reagent, ethyl orange is preferred, though the pH indicating reagent is not limited to this.

The determination of pH of a sample to be assayed with use of a pH indicating reagent can be carried out in the same manner as that in the conventional case, for example, by optically analyzing a color exhibited after the sample to be assayed and a protein indicating reagent are brought into contact with each other. As a specific form, the determination of pH can be carried out in the same manner as that of the optical analysis with use of the protein indicating reagent described above. The pH indicating reagent to be brought into contact with the sample to be assayed is usually 0.01 mg to 1 mg with respect to 1 mL of the sample to be assayed, and preferably 0.02 mg to 0.5 mg with respect to 1 mL of the sample to be assayed, from the viewpoint of improving the accuracy of the protein concentration assay with use of the protein indicating reagent and the viewpoint of economic efficiency.

[Protein Concentration Assay]

The "protein concentration assay" as described herein refers to assay of a concentration of protein in the sample to be assayed. This encompasses, for example, specifically determining a concentration of protein in a sample to be assayed (e.g., making an assay to determine that the concentration of protein in a sample to be assayed is xx μg/mL); determining that a concentration of protein in a sample to be assayed falls in a certain range (e.g., making an assay to determine that a concentration of protein in a sample to be assayed is xx to yy μg/mL); determining whether or not a concentration of protein in a sample to be assayed exceeds a predetermined threshold value (e.g., making an assay to determine that a concentration of protein in a sample to be assayed is xx μg/mL (a threshold value) or more (less)); and determining whether or not a concentration of protein in a sample to be assayed corresponds to either one of a positive and a negative that are set based on a predetermined reference value (e.g., making an assay to determine that the sample to be assayed is positive (negative)), though it is not limited to these.

The "protein concentration assay" in the assay method of the present disclosure is, for example, to correct the result of optical analysis of the color exhibited after the sample to be assayed and the protein indicating reagent are brought into contact with each other, as required based on the result of measurement of pH of the sample to be assayed, in one embodiment. The correction of the result of the optical analysis based on the value of the measured pH can be performed according to data for protein concentration assay that are prepared preliminarily with use of the protein indicating reagent and test samples.

[Data for Protein Concentration Assay]

The "data for protein concentration assay" as described herein refers to data containing information showing the way to assay a protein concentration according to the value of pH of a sample. The way of assay includes the assay method and the assay reference. The assay method can be represented by, for example, data showing a formula for converting a measured value into an assay value or a concentration value of optical analysis, coefficients for the formula, and the like. The assay reference can be represented by, for example, data showing a range or a threshold value of the measured value or the concentration value, which is used as reference for assay. The data for protein concentration assay include data for correcting a result of optical analysis with use of a protein indicating reagent, or assay of a protein concentration obtained from the result of optical analysis based on the pH of the measured solution. In other words, the data for protein concentration assay can be used to correct the result of analysis with use of a protein indicating reagent depending on pH where the protein indicating reagent could exhibit a color that corresponds to, not an actual protein concentration, but a false protein concentration, depending on a value of pH of a sample to be assayed. One exemplary embodiment of the data for protein concentration assay is data in which a method for calibrating a result of optical analysis of a protein indicating reagent, assay reference for the same, etc., are set as to each of predetermined pH ranges. For example, values (e.g., conversion coefficients) that are used for converting a value obtained as a result of optical analysis (e.g., an absorbance of a protein indicating reagent having been in contact with a sample) into a protein concentration of the sample or an assay value thereof, and that are set as to predetermined pH ranges, respectively, can be included in the data for protein concentration assay. Such data for protein concentration assay can be prepared preliminarily.

An exemplary embodiment of the data for protein concentration assay is data that are used for calculating a protein concentration of the sample from the result of optical analysis, and that are set according to pH of the sample. More specifically, data used as the data for protein concentration assay may be data that define a method of calculating a concentration of protein in the sample by at least using two parameters composed of a measured value of pH and the result of optical analysis. A specific example of the present embodiment is data in which methods (e.g., calibration formula) for calibrating protein concentrations determined with use of a protein indicating reagent are set as to predetermined pH ranges, respectively (Table 1 below). In the present embodiment, a protein concentration of a sample to be assayed after the calibration can be output as a result of assay. It should be noted that numerical values in Table 1 below are merely examples and do not limit the present disclosure at all.

TABLE 1

| Measured pH value | Way of assay (protein concentration C of sample to be assayed) |
|---|---|
| pH < 3.3 | C = 0.7 × (protein concentration determined by spectroscopic analysis) |
| 3.3 ≤ pH < 3.4 | C = 0.9 × (protein concentration determined by spectroscopic analysis) |
| 3.4 ≤ pH < 3.5 | C = (protein concentration determined by spectroscopic analysis) |
| 3.6 ≤ pH < 3.6 | C = 1.1 × (protein concentration determined by spectroscopic analysis) |
| 3.6 ≤ pH | C = 1.2 × (protein concentration determined by spectroscopic analysis) |

In the example shown in Table 1 above, the coefficients for correcting a value of a protein concentration obtained from a result of an optical analysis are recorded, with correspondence thereof to a plurality of pH ranges, respectively. Thus, by recording correction coefficients corresponding to values of pH, more accurate assay of a protein concentration, with a difference of pH being taken into consideration, is enabled. An exemplary modification of the above described embodiment can be to record calibration data (e.g., data indicating calibration curves) used for calculating a protein concentration from a result of optical analysis, as to each pH range.

Another exemplary embodiment of the data for protein concentration assay is data that are used as a reference when an assayed value is calculated based on the result of optical analysis and that are set according to values of pH of the sample. More specifically, data that are used as reference when whether or not the protein concentration of the sample falls in a predetermined concentration range is determined at least with use of the two parameters of the measured pH value and the result of optical analysis can be used as the data for protein concentration assay. A specific example of the present embodiment is data that include absorbance values (protein indicating reagent) that are used as reference for determination of positivity/negativity regarding a protein concentration, which are defined as to predetermined pH ranges, respectively (Table 2 below). In the present embodiment, determination of positivity or negativity of a sample to be assayed can be output as an assay result, according to the defined data. In the present embodiment, further, a protein concentration of a sample to be assayed can be assayed without conversion of an optical analysis value (absorbance) obtained as to a protein indicating reagent into a protein concentration. It should be noted that numerical values shown in Table 2 below are merely examples and do not limit the present disclosure at all.

In the example shown in Table 2, information indicating ranges of results of optical analysis (e.g., absorbance) that lead to determination of positivity, and information indicating ranges of results of optical analysis (e.g., absorbance) that lead to determination of negativity, are recorded, with correspondence thereof to a plurality of pH ranges, respectively. Thus, by recording threshold values for determination of positivity/negativity with correspondence thereof to data showing ranges of pH values, respectively, an appropriate assay of a protein concentration according to pH of a sample is enabled.

In one embodiment, the data for protein concentration assay may include data that define a normal range of pH values. This makes it possible to determine whether or not a measured value of pH of a sample is beyond a range in which accurate assay is allowed. More specifically, the data for protein concentration assay may include data that define predetermined low values and/or high values of pH among measured pH values as abnormal pH values. Examples of the same include data showing that a sample to be assayed that should exhibit pH in a predetermined range has actually a pH abnormally on an acidic side or abnormally on an alkaline side (Table 3 below). The use of such data allows abnormality of a sample to be assayed to be output as an assay result. Such an assay, for example, allows a sample having an abnormal value of pH to be detected at the same time in the case where biological samples are dealt with. The present embodiment can be combined with the above described two embodiments. It should be noted that the numerical values in Table 3 below are merely examples and do not limit the present disclosure at all.

TABLE 2

| Measured pH value | Way of assay (positivity/negativity of sample to be assayed) |
|---|---|
| pH < 3.3 | Positive when absorbance is 0.55 or more, negative when absorbance is less than 0.55 |
| 3.3 ≤ pH < 3.4 | Positive when absorbance is 0.56 or more, negative when absorbance is less than 0.56 |
| 3.4 ≤ pH < 3.5 | Positive when absorbance is 0.58 or more, negative when absorbance is less than 0.58 |
| 3.5 ≤ pH < 3.6 | Positive when absorbance is 0.59 or more, negative when absorbance is less than 0.59 |
| 3.65 ≤ pH | Positive when absorbance is 0.60 or more, negative when absorbance is less than 0.60 |

TABLE 3

| Measured pH value | Way of assay (protein concentration C of sample to be assayed) |
|---|---|
| pH < 3.3 | pH value is abnormal (acidic) |
| 3.3 ≤ pH < 3.8 | C = 0.85 × (protein concentration determined by spectroscopic analysis) |
| 3.8 ≤ pH < 4.2 | C = (protein concentration determined by spectroscopic analysis) |
| 4.2 ≤ pH < 4.6 | C = 1.5 × (protein concentration determined by spectroscopic analysis) |
| 4.6 ≤ pH | pH value is abnormal (alkaline) |

The data for protein concentration assay can be prepared according to assay purposes. It should be noted that parameters used for the data for protein concentration assay may include at least two of the measured pH value and the result of optical analysis. Three or more parameters including other parameters than these parameters may be used in the data for protein concentration assay.

By preliminarily preparing the data for protein concentration assay as described above and recording the same in an analyzer or the like, the protein concentration assay is enabled with respect to a sample, depending on a value of pH. The data for protein concentration assay can be prepared, for example, based on values obtained by optically analyzing a standard sample having a known protein concentration under various pH conditions. For example, as to each of a plurality of pH values or pH ranges, a value indicating relationship between results (e.g., absorbance) of optical analysis of a standard sample and protein concentrations of the standard sample is calculated, and this value is used as the data for protein concentration assay. In other words, it is possible that data for converting a value measured by optical analysis of a protein indicating reagent into a protein concentration value or a protein concentration assay value are generated as to a plurality of pH values or pH ranges, and the data are recorded as the data for protein concentration assay. It should be noted that the data for protein concentration assay are not limited to those described above.

[Sample to be Assayed]

The sample to be assayed by the assay method of the present disclosure is not limited particularly, and examples of the same include a biological sample, a biochemical sample, and an environmental sample. Examples of the biological sample include body fluid, urine, blood, and saliva.

[Analysis Tool]

In the assay method of the present disclosure, both of the contact between a sample to be assayed and a protein indicating reagent, and the pH measurement with respect to the sample with use of a pH indicating reagent, can be carried out at a reagent layer on a reagent strip, as described above. The present disclosure in another aspect, therefore, relates to an analysis tool having a reagent layer containing a protein indicating reagent, and a reagent layer containing a pH indicating reagent, on a substrate (hereinafter this analysis tool is referred to as an "analysis tool of the present disclosure" as well). The assay method of the present disclosure can be performed with use of the analysis tool of the present disclosure.

In the analysis tool of the present disclosure, the reagent layer containing the protein indicating reagent and the reagent layer containing the pH indicating reagent may be two individual reagent layers. Alternatively, the protein indicating reagent and the pH indicating reagent may be provided in one and the same reagent layer. In this case, the color of the protein indicating reagent and the color of the pH indicating reagent can be detected by optical analysis, at different wavelengths, respectively. Therefore, the protein indicating reagent and the pH indicating reagent preferably exhibit colors at different wavelengths, respectively, and have smaller influences exerted to each other.

Therefore, an exemplary first embodiment of the analysis tool of the present disclosure is an analysis tool having a substrate and a plurality of reagent layers formed on the substrate, wherein the reagent layers are a reagent layer A, containing a protein indicating reagent whose color varies with pH and a protein concentration, and a reagent layer B, containing a pH indicating reagent, wherein the reagent layers A and B contain a buffer so as to have an identical buffer condition. An exemplary second embodiment of the present disclosure is an analysis tool having a substrate and a reagent layer formed on the substrate, wherein the reagent layer contains a protein indicating reagent whose color varies with a value of pH and a protein concentration, and a pH indicating reagent. In this way, by providing a reagent layer containing a protein indicating reagent and a pH indicating reagent, the number of reagent layers can be decreased, whereby the analysis tool can be reduced in size. It should be noted that in the first and second embodiments, a pH indicating reagent that is not prone to being influenced by the protein concentration in a solution is used preferably.

In the analysis tools of the first and second embodiments, as to the "protein indicating reagent whose color varies with a value of pH and a protein concentration," the "pH indicating reagent that is not prone to being influenced by the protein concentration in a solution," and the "buffer" those that can be used are explained above as to the assay method of the present disclosure.

The analysis tool of the present disclosure may include a reagent layer other than the reagent layer containing a protein indicating reagent and the reagent layer containing a pH indicating reagent. The number of reagent layers is not limited particularly, and may be, for example, 1 to 15, preferably 1 to 10, and more preferably 1 to 8. The analysis tool of the present disclosure can be subjected to analysis by a conventionally known optical analyzer and allows the assay method of the present disclosure to be carried out with use of an analyzer of the present disclosure that will be described later.

Figure 1A:
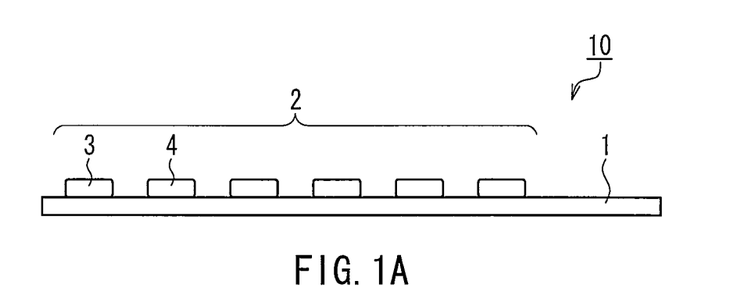
FIGS. 1A and 1B are a side view of an analysis tool 10 in one embodiment, and a top view of the same, respectively.
Figure 1B:
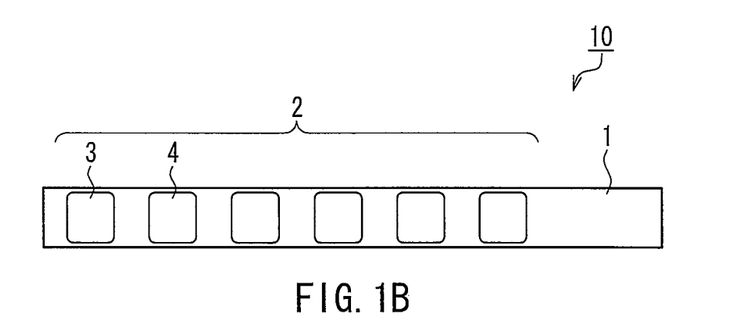

An exemplary analysis tool of the present disclosure is shown in FIG. 1. FIG. 1A is a side view, and FIG. 1B is a top view. In FIGS. 1A and 1B, the same members are denoted by the same reference numerals. In this sample analysis tool 10, six reagent layers 2 are formed on a strip-form substrate 1. The material of the substrate is not limited particularly and may be a resin, a metal, or glass. The color of the substrate is not limited particularly and may be any one of white, gray, black, a chromatic color, a transparent color, or the like. The size of the substrate is not limited particularly and is appropriately decided according to the test items, specifications of an analyzer used, and the like. The size of the substrate is, for example, 50 to 150 mm in length, 2 to 10 mm in width, and 0.1 to 1.0 mm in thickness. Each reagent layer 2 is formed by attaching a pad containing a predetermined reagent corresponding to a test item onto the substrate 1. Exemplary materials for the pad include filter paper, glass fiber filter paper, a knitted fabric, a woven fabric, a non-woven fabric, a membrane filter, and a porous resin sheet. The shape of each reagent layer 2 (pad) is not limited particularly and may be square, rectangular, circular, oval, or the like. The size of each reagent layer 2 (pad) is not limited particularly, and in the case where the shape is square, the size thereof is, for example, 2 to 10 mm in vertical and horizontal dimensions and 0.05 to 1.0 mm in thickness. The number of the reagent layers 2 can be increased/decreased according to test items. Six of these reagent layers 2 are arranged in series at constant intervals. This interval is not limited particularly and may be 1.0 to 100 mm, for example. At one end of the substrate 1 of this sample analysis tool (a right-side end as viewed in the drawing), no reagent layer 2 is provided, so that a space is left there, and the analysis tool can be handled with this part (holding part) being pinched between the tips of fingers.

In the case of the first embodiment of the analysis tool of the present disclosure, in FIG. 1, for example, the reagent layer 3 may be the reagent layer A containing a protein indicating reagent, and the reagent layer 4 may be the reagent layer B containing a pH indicating reagent. In the case of the second embodiment of the analysis tool of the present disclosure, in FIG. 1, for example, the reagent layer 3 or 4 may be the reagent layer containing a protein indicating reagent and a pH indicating reagent. It should be noted that positions of the reagent layers A and B, or a position of the reagent layer containing a protein indicating reagent and a pH indicating reagent, is not limited to that shown in FIG. 1.

[Analyzer]

The present disclosure in still another aspect relates to an analyzer that is capable of performing the assay method of the present disclosure (hereinafter referred to as an "analyzer of the present disclosure" as well). An exemplary one embodiment of the analyzer of the present disclosure is an analyzer that includes:

a measurement section that optically analyzes a color exhibited after a sample and a protein indicating reagent are brought into contact with each other;

a measurement section that measures pH of the sample;

an assay section that assays a concentration of protein in the sample based on the result of the optical analysis, the measured value of pH, and data for protein concentration assay; and an output section that outputs data after assay, wherein the protein indicating reagent is a protein indicating reagent whose color varies with pH and a concentration of protein, and the data for protein concentration assay include information indicating a way to assay the result of the optical analysis corresponding to the measured value of pH.

In the analyzer of the present embodiment, those explained above regarding the assay method of the present disclosure can be used as the "protein indicating reagent whose color varies with pH and a concentration of protein" and the data for protein concentration assay,"

In the analyzer of the present embodiment, the measurement section that measures pH may be a measurement section that measures pH of a sample to be assayed with use of a pH meter, or alternatively, a measurement section that performs optical analysis of the pH indicating reagent. In the latter case, the measurement section that optically analyzes a protein indicating reagent and the measurement section that performs optical analysis of a pH indicating reagent may be formed as one and the same measurement section.

In the analyzer of the present embodiment, the measurement section that optically analyzes a protein indicating reagent and the measurement section that performs optical analysis of a pH indicating reagent may be formed as one and the same measurement section. Additionally, the measurement section that optically analyzes a protein indicating reagent and the measurement section that performs optical analysis of a pH indicating reagent may be those that perform optical analysis of a liquid or those that perform optical analysis of reagent layers of the analyzer. Therefore, the analyzer of the present disclosure in another embodiment is an analyzer that performs the assay method of the present disclosure by using the analysis tool of the present disclosure.

Figure 2:
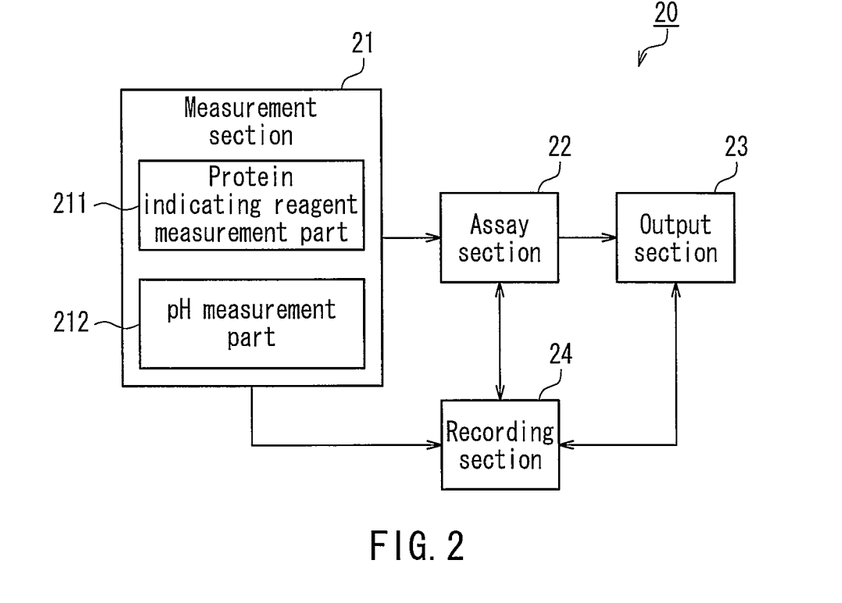
FIG. 2 is a functional block diagram showing an exemplary configuration of an analyzer in one embodiment.

FIG. 2 is a functional block diagram showing an exemplary configuration according to one embodiment of the analyzer of the present disclosure. An analyzer 20 shown in FIG. 2 is a device that provides measurements regarding a protein indicating reagent and pH, and assays of a protein concentration. The analyzer 20 includes a measurement section 21, an assay section 22, and an output section 23, and additionally, a recording section 24. The measurement section 21 includes a measurement part 211 with respect to a protein indicating reagent and a pH measurement part 212. The measurement part 211 performs optical analysis with use of a protein indicating reagent. As described above, in the case where the measurement by the pH measurement part 212 is measurement by optical analysis, the measurement parts 211 and 212 may be formed as one measurement part. A result of the optical analysis with use of a protein indicating reagent and a measured pH value obtained by the measurement section 21 may be stored in the recording section 24. The assay section 22 performs assays according to the results of an optical analysis with use of a protein indication reagent and the measured pH value obtained by the measurement section 21 and the data for protein concentration assay stored in the recording section 24. Here, the data for protein concentration assay can be prepared preliminarily and stored in the recording section 24. The result of the assay is recorded in the recording section 24 and/or is output to the output section 23. Examples of the output section 23 include a display section, a printing section for printing the same, and a transmission section that transmits the same to outside.

(Measurement Section)

In the example shown in FIG. 2, the measurement part 211 with respect to a protein indicating reagent and the pH measurement part 212 are formed as one and the same measurement part. In this case, for example, the measurement section 21 measures an absorbance, a reflectance, a transmittance, or the like by detecting transmitted light or scattering light of each reagent layer 2 of the analysis tool as shown in FIG. 1. For example, a sample is dropped onto a reagent layer containing a protein indicating reagent and a reagent layer containing a pH indicating reagent, and absorbances of the same are measured, whereby the measurement with respect to the protein indicating reagent in contact with a sample and the measurement of pH of the sample can be carried out. In the case where a protein indicating reagent and a pH indicating reagent are contained in one reagent layer, the measurement section 21 is capable of measuring an absorbance, a transmittance, or a reflectance as to each of a wavelength (or a band) corresponding to the protein indicating reagent and a wavelength (or a band) corresponding to the pH indicating reagent, based on transmitted light or scattering light of the one reagent layer. Thus, as to one reagent layer, lights at wavelengths or in bands corresponding to a protein indicating reagent and a pH indicating reagent, respectively, may be analyzed optically, whereby information about protein in a sample and pH of the sample can be obtained.

(Assay Section)

The method of assay with use of the data for protein concentration assay at the assay section 22 may be performed as explained in the description regarding the assay method of the present disclosure. In one embodiment, the data for protein concentration assay include data that are used for calculating when a protein concentration of the sample is derived from the result of optical analysis and data that correspond to values of pH of the sample (see, for example, Table 1 shown above); and thus, the assay section can calculate a protein concentration of the sample based on the calculation data by using the measured pH value and the result of optical analysis. The assay section determines, for example, to which pH range the pH value of the sample belongs, and obtains, as calculation data, a correction coefficient corresponding to the range to which the pH value of the sample belongs. In this case, the assay section can correct a protein concentration obtained from the result of optical analysis by using the correction coefficient or a formula including the correction coefficient. This makes it possible to more accurately assay a protein concentration, by taking fluctuations in results of optical analyses due to pH of samples into consideration.

In another embodiment, the data for protein concentration assay include reference data that are used as reference when an assay value is calculated based on the result of optical analysis and that correspond to pH values of the sample (see, for example, Table 2 shown above); and, the assay section can calculate the assay value with reference to the reference data based on the measured pH value and the result of optical analysis. The assay section can determine to which pH range the pH value of the sample belongs, and obtain, as reference data, a threshold value for determination about negativity/positivity corresponding to the range to which the pH value of the sample belongs. In this case, the assay section compares a value, such as an absorbance obtained as the result of optical analysis, and a threshold value for the determination of negativity/positivity and thus determines whether the protein concentration of the sample is positive or negative. This makes it possible to more accurately assay a protein concentration by taking fluctuations in results of optical analysis due to pH of samples into consideration.

Further, the data for protein concentration assay include data for defining a normal range of pH measured (see, for example, Table 3 shown above), and the assay section can perform assays according to the foregoing definition based on the measured pH value. In the case where, for example, the assay section determines that the pH value of the sample does not fall in the normal pH range indicated by the data for protein concentration assay, the assay section can output a response to the effect that it is impossible to perform an accurate assay, or to the effect that the assay result is less reliable. This makes it possible to detect an abnormality in pH of a sample and output it. However, the assay by the assay section 22 is not limited to this.

(Exemplary Modification of Measurement Section)

Figure 3:
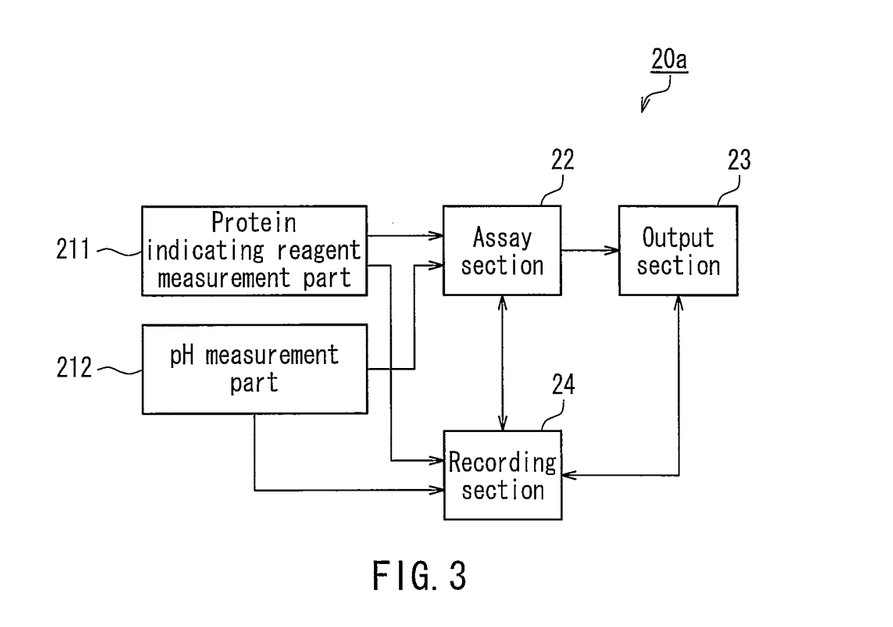
FIG. 3 is a functional block diagram showing another exemplary configuration of an analyzer in one embodiment.

FIG. 3 is a functional block diagram showing a configuration of an exemplary modification of the analyzer 20 shown in FIG. 2. In an analyzer 20a shown in FIG. 3, a measurement part 211 with respect to a protein indicating reagent, and a pH measurement part 212 are provided independently from each other. In the example shown in FIG. 3, the measurement part 211 is a meter that measures a color by optical analysis as is the case with the measurement part 211 of the analyzer 20 shown in FIG. 2, and the measurement part 212 is a pH meter. Thus, by providing the measurement system with respect to a protein indicating reagent and the measurement system for measuring pH of a sample separately from each other, the reliability of the pH measurement can be improved. An example of the pH meter as the measurement part 212 is a pH meter that uses the glass electrode method, provided with a glass electrode and a reference electrode, though the structure of the pH meter is not limited particularly.

The analyzers 20 and 20a shown in FIGS. 2 and 3 may have configurations in which the measurement part 211, the measurement part 212, the assay section 22, the output section 23, and the recording section 24 are independent from one another and connected, or alternatively, may have configurations in which all or a part of these are integrally provided. The assay section 22 can be realized with a computer provided in the analyzer 20 or 20a. For example, the function of the assay section 22 can be realized by a processor in the analyzer 20 or 20a executing a predetermined program. The recording section 24 can be realized with a recording medium such as a memory provided in the analyzer 20 or 20a, or a storage accessible from the analyzer 20 or 20a.

(Exemplary Operation)

Figure 4:
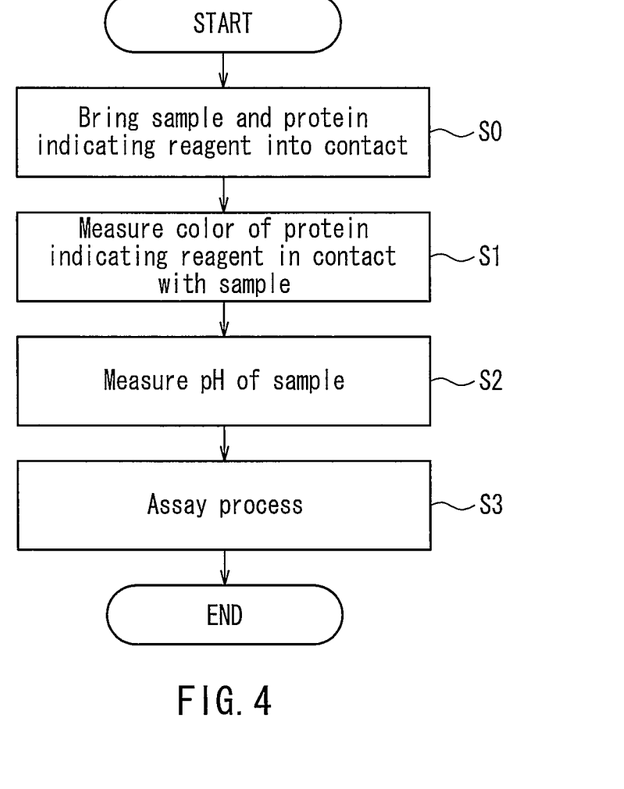
FIG. 4 is a flowchart showing an exemplary operation of an analyzer in one embodiment.

FIG. 4 shows a flowchart showing an exemplary operation of the analyzer 20 or 20a (hereinafter simply referred to as the "analyzer") shown in FIG. 2 or 3. In the example shown in FIG. 4, first, the processor in the analyzer controls the measurement part 211 so that a sample and a protein indicating reagent are brought into contact with each other (S0). The measurement part 211 determines a color of the protein indicating reagent in contact with the sample by optical analysis (S1). For example, the measurement section 211 causes the contact to occur by dropping the sample onto a reagent layer of the analysis tool shown in FIG. 1 that contains the protein indicating reagent. In this case, the measurement part 211 can optically analyze the color exhibited by the protein indicating reagent in contact with the sample by measuring an absorbance, a reflectance, or a transmittance of the reagent layer. The result of optical analysis (e.g., absorbance) obtained by the measurement part 211 is transmitted to the assay section 22.

At Step S2, the processor of the analyzer controls the measurement part 211 to measure pH of the sample. In the analyzer 20 shown in FIG. 2, the measurement part 212 can measure pH of the sample by optically analyzing light from the reagent layer containing the pH indicating reagent onto which the sample has been dropped. The analyzer 20a shown in FIG. 3 can determine pH of a sample with the pH measurement part 212, by, for example, measurement with use of the glass electrode method. The value of pH of the sample thus measured is transmitted to the assay section 22.

The assay section 22 executes a protein concentration assay process corresponding to the pH of the sample, and uses the result of optical analysis with the protein indicating reagent obtained at Step S1, the pH of the sample measured at Step S2, and the data for protein concentration assay recorded in the recording section 24 (S3). More specifically, the assay section 22 obtains the data for protein concentration assay corresponding to the pH of the sample measured at Step S2 from the recording section 24 and subjects the result of optical analysis with use of the protein indicating reagent obtained at S1 or information obtained from the result of optical analysis to correction according to the pH, by using the data for protein concentration assay. The assay section 22 may generate the corrected result of optical analysis, the corrected information about the protein concentration as an assay result, or an assay value based on the result of optical analysis or the protein concentration (e.g., a value indicating positivity or negativity) as an assay result. The assay section 22 calculates a protein concentration of a sample itself, a range to which the protein concentration belongs, a resulting comparison between the protein concentration and a predetermined threshold value, information indicating positivity or negativity, or the like, as the assay result. The output section 23 outputs an evaluation result generated by the assay section 22. The output can be carried out in a form of, for example, display on a display device provided in the analyzer, printing by a printer, audio output from a speaker, transmission of data via a network, or a combination of any of these.

Figure 5:
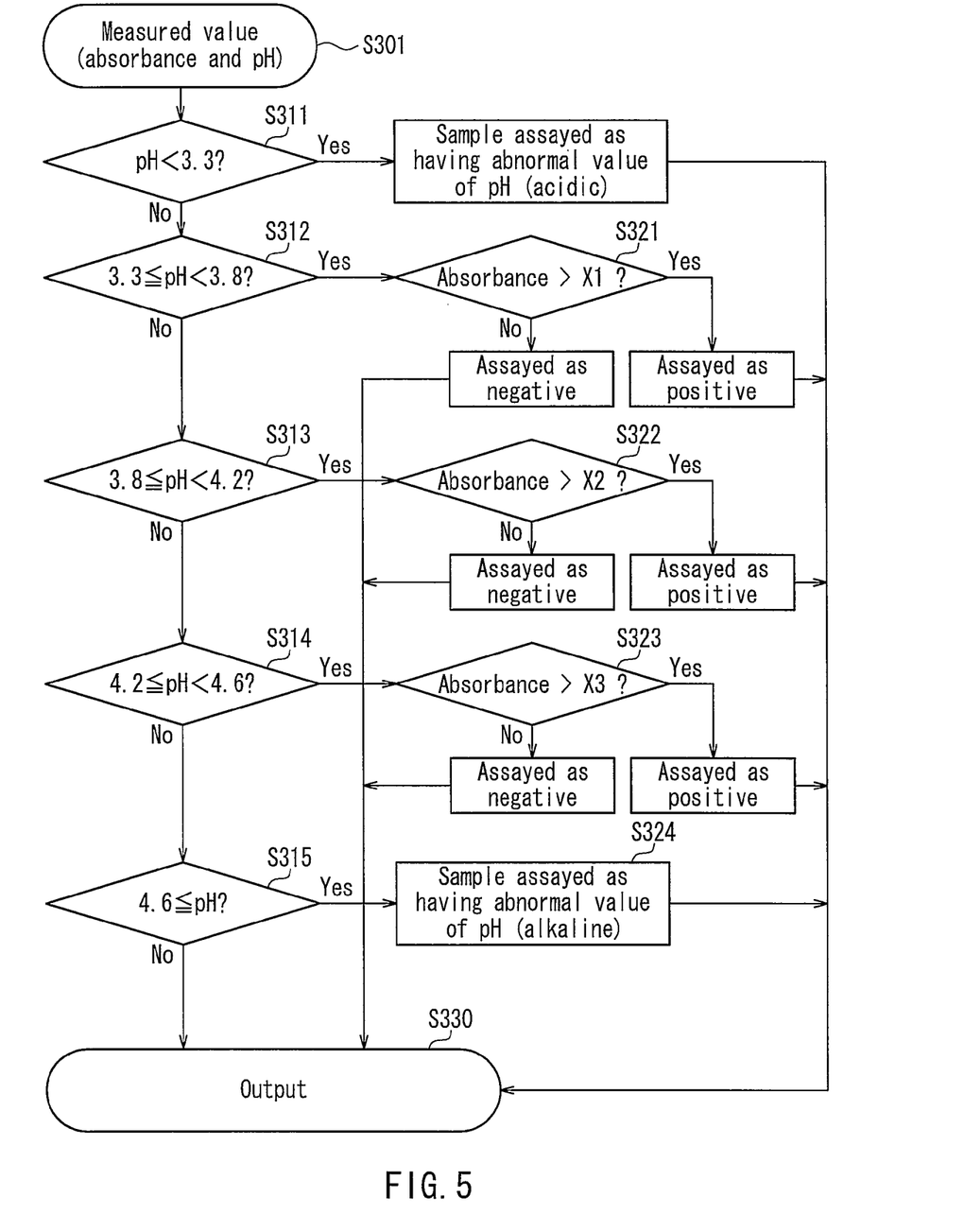
FIG. 5 is a flowchart showing another exemplary operation of an analyzer in one embodiment.

FIG. 5 is an exemplary flowchart showing an exemplary operation of the assay section 22 at Step S3 shown in FIG. 4. The assay section 22 obtains a measured value as a result of optical analysis (absorbance) with use of the protein indicating reagent and a measured pH value (S301). Next, at the assay section 22, first, an assay definition to be applied, corresponding to the measured pH value, is selected (Steps S311 to 315). Here, as an example, a way of assay (assay method or assay reference) corresponding to the measured pH value is extracted from those defined by the data for protein concentration assay recorded in the recording section 24. Table 4 shown below shows an exemplary way of assay defined by the data for protein concentration assay. In Table 4 below, the way to assay is recorded with correspondence to pH ranges.

TABLE 4

| pH value | Way of assay |
|---|---|
| pH < 3.3 | pH value is abnormal (acidic) |
| 3.3 ≤ pH < 3.8 | Reference value for determination of positivity/negativity = X1 |
| 3.8 ≤ pH < 4.2 | Reference value for determination of positivity/negativity = X2 |
| 4.2 ≤ pH < 4.6 | Reference value for determination of positivity/negativity = X3 |
| 4.6 ≤ pH | pH value is abnormal (alkaline) |

For example, in the case where pH is less than 3.3 (Yes at S311), the assay section 22 extracts data indicating that the pH value is abnormal (acidic), as data indicating a way of assay, from the data for protein concentration assay, and outputs this as an assay result. In the case where pH is 3.3 or more and less than 3.8 (Yes at Step S312), the assay section 22 extracts a reference value X1 form the data for protein concentration assay, and compares X1 and an absorbance as a result of optical analysis with use of the protein indicating reagent (S321). For example, the assay section 22 can determine that the sample is negative in the case where the absorbance is greater than X1, or determines that the sample is positive in the case where the absorbance does not exceed X1. Likewise, the assay section 22 determines negativity/positivity with reference to X2 (S322) in the case where pH is 3.8 or more and less than 4.2 (Yes at Step S313), and determines negativity/positivity with reference to X3 (S323) in the case where pH is 4.2 or more and less than 4.6 (Yes at Step S314). In the case where pH is 4.6 or more, the assay section 22 determines that the sample exhibits an abnormal pH value (S324) based on the data indicating "pH value is abnormal (alkaline)" in the data for protein concentration assay, and outputs the same (S330). The assay section 22 thus determines to which range the pH measured at Steps S312 to S315 belongs, determines an assay reference based on the result of the foregoing determination, and determines whether or not an abnormality exists in pH (S324) or whether the sample is positive or negative (S321 to S323). The result of determination is output as a result of assay (S330).

With the above-described exemplary operation, an appropriate way of assay is selected according to pH of a sample measured, and therefore, an assay result corrected appropriately according to the pH can be obtained. It should be noted that the operation of the analyzer according to the present disclosure is not limited to that described above, with reference to FIGS. 4 and 5. For example, in FIG. 4, the order of execution of Steps S1 and S2 may be reversed. Further, regarding Steps S321 to 323 shown in FIG. 5, a process of calculation by a calculating method corresponding to pH at which the protein concentration is measured may be carried out instead of, or in addition to, the process for determining negativity/positivity by comparison between an absorbance and a reference value.

It should be noted that the present disclosure also encompasses an assay program that causes a computer for outputting a result of an assay of a sample to execute the processes of obtaining a result of an optical analysis with use of a protein indicating reagent and pH of the sample to be assayed; accessing a recording section that has preliminarily recorded the data for protein concentration assay; selecting an assay method or an assay reference corresponding to the result of optical analysis with use of the protein indicating reagent and the measured pH value, and performing assay; and outputting the obtained assay result. The present disclosure also encompasses a non-transitory recording medium storing the foregoing program and an analyzer in which this program is installed.

For example, a protein concentration assay program that causes a computer to execute a process of assaying a protein concentration of a sample is also one embodiment of the present disclosure, the program causing the computer to execute the processes of inputting a result of optical analysis of a color after the sample and a protein indicating reagent are brought into contact with each other, and a measured pH value of the sample; and assaying a protein concentration of the sample based on the result of optical analysis and the measured pH value, as well as the data for protein concentration assay, wherein the data for protein concentration assay include information about a way for assaying the result of optical analysis corresponding to the measured pH value.

A program for controlling an analyzer is also one embodiment of the present disclosure, the program causing the analyzer to execute: a process of causing a measurement section of the analyzer to optically analyze a color after a sample and a protein indicating reagent are brought into contact with each other; a process of causing the measurement section of the analyzer to measure pH; an assay process of assaying a protein concentration of the sample based on the result of optical analysis, the measured pH value, and the data for protein concentration assay; and an output process of outputting the data after the assay, wherein the data for protein concentration assay include information about a way of assaying the result of optical analysis corresponding to the measured pH value.

(Specific Example of Analyzer)

Figure 6:
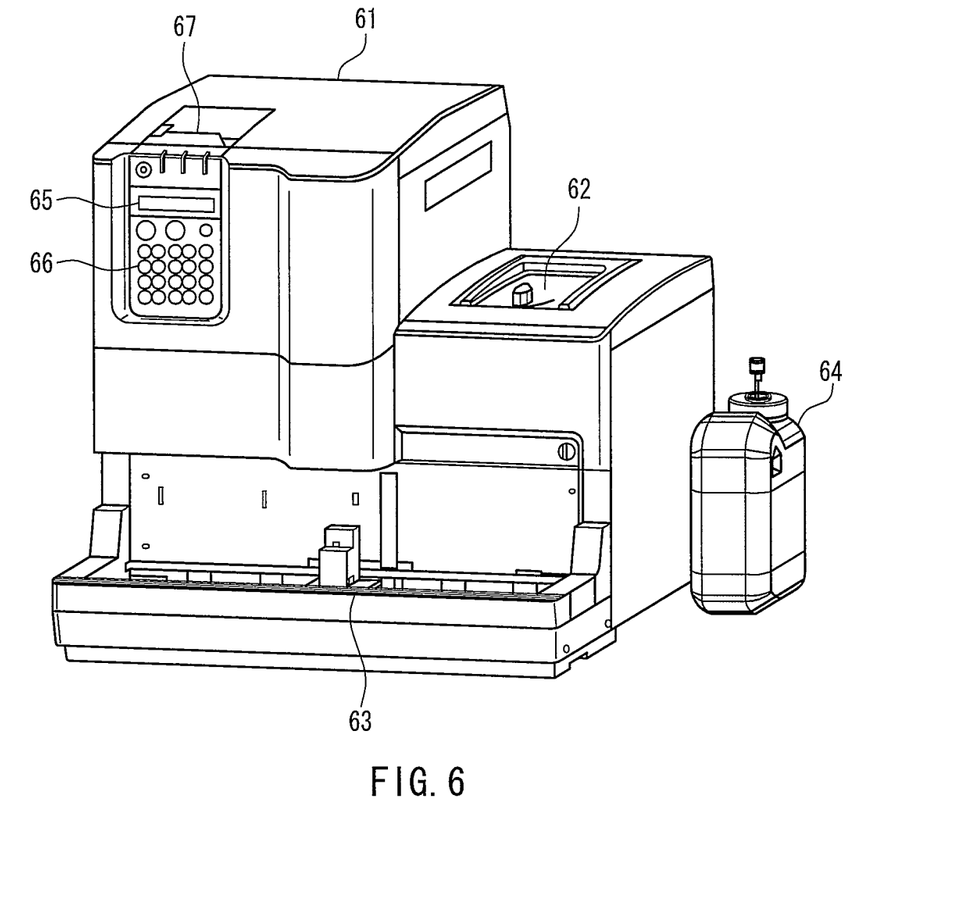
FIG. 6 is an external appearance perspective view of an automatic urine chemical analyzer in which a urine analyzer of one embodiment is used.

FIG. 6 is an external appearance perspective view of an automatic urine chemical analyzer in which a urine analyzer as a specific example of the analyzer 20 is used. The automatic urine chemical analyzer shown in FIG. 6 includes a main body 61, a test strip supply section 62, a sample supply section 63, and a bottle unit 64. The main body 61 includes a display section 65, an operation section 66, and a printer section 67.

In the main body 61, a movable nozzle is provided, which sucks urine from a container mounted on the sample supply section 63 that contains urine as a specimen (sample), and drops, or spots, the urine onto a plurality of reagent pads (exemplary reagent layers) provided on a test strip (an exemplary analysis tool) transferred to a predetermined position inside the main body 61.

The reagent pads onto which urine has been dropped are subjected to measurement of colors thereof and the like by an optical system (corresponding to the measurement section) provided in the main body 61, and based on the measurement results, the test result is determined and is outputted by printing by the printer section 67. One of the reagent pads contains a protein indicating reagent and a pH indicating reagent. The measurement section executes optical analysis at a wavelength corresponding to the protein indicating reagent and optical analysis at a wavelength corresponding to the pH indicating reagent. Thus, measurement results can be obtained with respect to the protein indicating reagent and the pH indicating reagent. This allows the measured value regarding protein in urine or the assay value to be corrected to an appropriate value.

Though not shown, the automatic urine chemical analyzer can include a CPU, a memory (e.g., ROM (read only memory), a RAM (random access memory), a HD (hard disk), etc.), a motor driving section, and a valve driving section. The CPU operates according to a program recorded in a memory. In the memory, the above described data for protein concentration assay are recorded. The CPU controls the motor driving section and the valve driving section. The motor driving section, controlled by the CPU, drives a plurality of pumps for causing the sucking or cleaning by the nozzle, etc. to be performed. A valve driving section, controlled by the CPU, drives a plurality of valves for causing the sucking or cleaning by the nozzle, etc. to be performed.

In this way, the analyzer may have a configuration that includes a means for providing a reagent, a means for providing a sample, a means for bringing a protein indicating reagent as one of reagents into contact with a sample, a means for measuring pH of a sample, a means for measuring a color of a reagent in contact with a sample, a means for analyzing a measurement result, and a means for controlling these. It should be noted that the analyzer is not limited to the above described example. For example, a pH meter for measuring pH of urine as a sample may be provided. The pH meter has an exemplary configuration of measuring pH of a sample by dipping a glass electrode and a reference electrode thereof in urine as the sample and measuring a voltage across the electrodes.

Hereinafter the present disclosure is further explained by way of illustrative examples.

EXAMPLE

Protein Concentration Assay of BSA Solution

Example 1 and Comparative Example 1

Twelve types of BSA solutions shown below were prepared with use of tetrabromophenol blue as a protein indicating reagent. Absorbances (620 nm) of these BSA solutions were measured by a spectrophotometer (manufactured by JASCO Corporation). The results are shown in Table 5 below.

[pH Adjustment and Measurement]

The adjustment of pH was carried out with use of NaOH (5N). The pH was measured with respect to an object at 25° C. with use of a pH meter (HORIBA Ltd., trade name: F23). This applies to Examples and Comparative Examples described below.

[BSA Solution Compositions]
  0.1 M malic acid (pH 3.7/4.1/4.5)
  1.5 mg/dL tetrabromophenol blue (manufactured by NACALAI TESQUE, INC.)
  BSA (bovine serum albumin, manufactured by Sigma-Aldrich Co. LLC.) (0/10/25/50 mg/dL)

TABLE 5

| | Absorbance | | | |
|---|---|---|---|---|
| | 0 mg/dL | 10 mg/dL | 25 mg/dL | 50 mg/dL |
| pH 3.7 | 0.42 | 0.66 | 0.82 | 0.89 |
| pH 4.1 | 0.56 | 0.68 | 0.83 | 0.88 |
| pH 4.5 | 0.68 | 0.73 | 0.85 | 0.90 |

Comparative Example 1

According to the data for the assay shown below that are based on absorbances of tetraburomophenol blue shown in Table 5 alone, whether each sample was positive or negative was determined, as to the protein concentrations of the BSA solutions shown in Table 5. It should be noted that it was assumed that the positivity as an assay result means that the protein concentration is 10 mg/dL or more and that the negativity as an assay result means that the protein concentration is less than 10 mg/dL. The results are shown in Table 6 below.

The data for assay:
  a sample is negative when the absorbance is less than 0.54 and is positive when the absorbance is 0.54 or more ("0.54" is an intermediate value between the absorbance of a solution having pH of 3.7 and containing 0 mg/dL of BSA, and the absorbance of a solution having pH of 3.7 and containing 10 mg/dL of BSA).

TABLE 6

| | Protein concentration | | | |
|---|---|---|---|---|
| | 0 mg/dL | 10 mg/dL | 25 mg/dL | 50 mg/dL |
| | Negative | | Positive | |
| pH 3.7 | Negative | Positive | Positive | Positive |
| pH 4.1 | Positive | Positive | Positive | Positive |
| pH 4.5 | Positive | Positive | Positive | Positive |

As shown in Table 6 above, when pH was 4.1 and 4.5, at which the protein indicating reagent exhibited high absorbances even though the protein concentration was 0 mg/dL, the samples that should have been determined to be negative were determined to be positive with reference to the absorbance at pH of 3.7 (a false positive occurred).

Example 1

According to the data for the assay shown below that are based on both the absorbances of tetraburomophenol blue shown in Table 5 and the pH of the BSA solutions, whether each sample was positive or negative was determined, as to the protein concentrations of the BSA solutions shown in Table 5. It should be noted that it was assumed that the positivity as an assay result means that the protein concentration is 10 mg/dL or more and that the negativity as an assay result means that the protein concentration is less than 10 mg/dL, as is the case with Comparative Example 1. The results are shown in Table 7 below.

The data for assay:

at pH of 3.7, a sample is negative when the absorbance is less than 0.54 and is positive when the absorbance is 0.54 or more ("0.54" is an intermediate value between the absorbance of a solution having pH of 3.7 and containing 0 mg/dL of BSA, and the absorbance of a solution having pH of 3.7 and containing 10 mg/dL of BSA);

at pH of 4.1, a sample is negative when the absorbance is less than 0.62 and is positive when the absorbance is 0.62 or more ("0.62" is an intermediate value between the absorbance of a solution having pH of 4.1 and containing 0 mg/dL of BSA, and the absorbance of a solution having pH of 4.1 and containing 10 mg/dL of BSA); and at pH of 4.5, a sample is negative when the absorbance is less than 0.70 and is positive when the absorbance is 0.70 or more ("0.70" is an intermediate value between the absorbance of a solution having pH of 4.5 and containing 0 mg/dL of BSA, and the absorbance of a solution having pH of 4.5 and containing 10 mg/dL of BSA).

TABLE 7

|  | Protein concentration | | | |
| --- | --- | --- | --- | --- |
|  | 0 mg/dL | 10 mg/dL | 25 mg/dL | 50 mg/dL |
|  | Negative | Positive | | |
| pH 3.7 | Negative | Positive | Positive | Positive |
| pH 4.1 | Negative | Positive | Positive | Positive |
| pH 4.5 | Negative | Positive | Positive | Positive |

As shown in Table 7 above, the assay carried out by taking pH into consideration did not lead to false positives at pH of 4.1 and 4.5 that occurred in Comparison Example 1. Thus, a highly accurate protein concentration assay was performed.

Protein Concentration Assay of BSA-Added Urine Samples

Example 2 and Comparative Example 2

BSA-added urine samples shown below were prepared by adding BSA to urine. Further, protein indicating reagent solutions shown below, as solutions of malic acid and tetrabromophenol blue, were prepared. The BSA-added urine samples and the protein indicating reagent solutions were mixed at a ratio of 1:1, whereby 15 types of mixed sample solutions were prepared. Absorbances (620 nm) of these mixed sample solutions were measured by a spectrophotometer (manufactured by JASCO Corporation). The results are shown in Table 8 below.

[BSA-Added Urine Sample Compositions]
  BSA (bovine serum albumin, manufactured by Sigma-Aldrich Co. LLC.) (0/5/10/15/20 mg/dL) was added to a urine sample

[Protein Indicating Reagent Solution Compositions]
  0.2 M malic acid (pH 3.7/4.1/4.5)
  3.0 mg/dL tetrabromophenol blue (manufactured by NACALAI TESQUE, INC.)

TABLE 8

|  | Absorbance | | | | |
| --- | --- | --- | --- | --- | --- |
|  | 0 mg/dL | 2.5 mg/dL | 5 mg/dL | 7.5 mg/dL | 10 mg/dL |
| pH 3.7 | 0.20 | 0.31 | 0.43 | 0.51 | 0.54 |
| pH 4.1 | 0.32 | 0.35 | 0.41 | 0.52 | 0.59 |
| pH 4.5 | 0.48 | 0.41 | 0.48 | 0.57 | 0.61 |

Comparative Example 2

According to the data for the assay shown below that are based on absorbances of tetraburomophenol blue shown in Table 8 alone, whether each sample was positive or negative was determined, as to the protein concentrations of the mixed sample solutions shown in Table 8. It should be noted that it was assumed that the positivity as an assay result means that the protein concentration is 10 mg/dL or more and that the negativity as an assay result means that the protein concentration is less than 10 mg/dL. The results are shown in Table 9 below.

The data for assay:

a sample is defined to be negative when the absorbance is less than 0.53 and is defined to be positive when the absorbance is 0.53 or more ("0.53" is an intermediate value between the absorbance of a solution having pH of 3.7 and containing 7.5 mg/dL of BSA, and the absorbance of a solution having pH of 3.7 and containing 10 mg/dL of BSA).

TABLE 9

|  | Added protein concentration | | | | |
| --- | --- | --- | --- | --- | --- |
|  | 0 mg/dL | 2.5 mg/dL | 5 mg/dL | 7.5 mg/dL | 10 mg/dL |
|  | Negative | | | | Positive |
| pH 3.7 | Negative | Negative | Negative | Negative | Positive |
| pH 4.1 | Negative | Negative | Negative | Negative | Positive |
| pH 4.5 | Negative | Negative | Negative | Positive | Positive |

As shown in Table 9, when pH was 4.5, the sample having a protein concentration of 7.5 mg/dL that should have been determined to be negative was determined to be positive (a false positive occurred).

Example 2

According to the data for the assay shown below that are based on both the absorbances of tetraburomophenol blue shown in Table 8 and the pH of the mixed sample solutions, whether each sample solution was positive or negative was determined, as to the protein concentrations of the mixed sample solutions shown in Table 8. It should be noted that it was assumed that the positivity as an assay result means that the protein concentration is 10 mg/dL or more and that the negativity as an assay result means that the protein concentration is less than 10 mg/dL, as is the case with Comparative Example 2. The results are shown in Table 10 below.

The data for assay:

at pH of 3.7, a mixed sample solution is defined to be negative when the absorbance is less than 0.53 and is defined to be positive when the absorbance is 0.53 or more ("0.53" is an intermediate value between the absorbance of a solution having pH of 3.7 and containing 7.5 mg/dL of BSA, and the absorbance of a solution having pH of 3.7 and containing 10 mg/dL of BSA);

at pH of 4.1, a mixed sample solution is defined to be negative when the absorbance is less than 0.55 and is defined to be positive when the absorbance is 0.55 or more ("0.55" is an intermediate value between the absorbance of a solution having pH of 4.1 and containing 7.5 mg/dL of BSA, and the absorbance of a solution having pH of 4.1 and containing 10 mg/dL of BSA); and at pH of 4.5, a mixed sample solution is defined to be negative when the absorbance is less than 0.59 and is defined to be positive when the absorbance is 0.59 or more ("0.59" is an intermediate value between the absorbance of a solution having pH of 4.5 and containing 7.5 mg/dL of BSA, and the absorbance of a solution having pH of 4.5 and containing 10 mg/dL of BSA).

TABLE 10

| | Added protein concentration | | | | |
|---|---|---|---|---|---|
| | 0 mg/dL | 2.5 mg/dL | 5 mg/dL | 7.5 mg/dL | 10 mg/dL |
| | | Negative | | | Positive |
| pH 3.7 | Negative | Negative | Negative | Negative | Positive |
| pH 4.1 | Negative | Negative | Negative | Negative | Positive |
| pH 4.5 | Negative | Negative | Negative | Negative | Positive |

As shown in Table 10 above, the assay carried out by taking pH into consideration did not lead to a false positive at pH of 4.5 that occurred in Comparison Example 2. Thus, a highly accurate protein concentration assay was performed.

pH Indicating Reagent not Prone to Being Influenced by Protein in Solution

Reference Example 1

Figure 7:
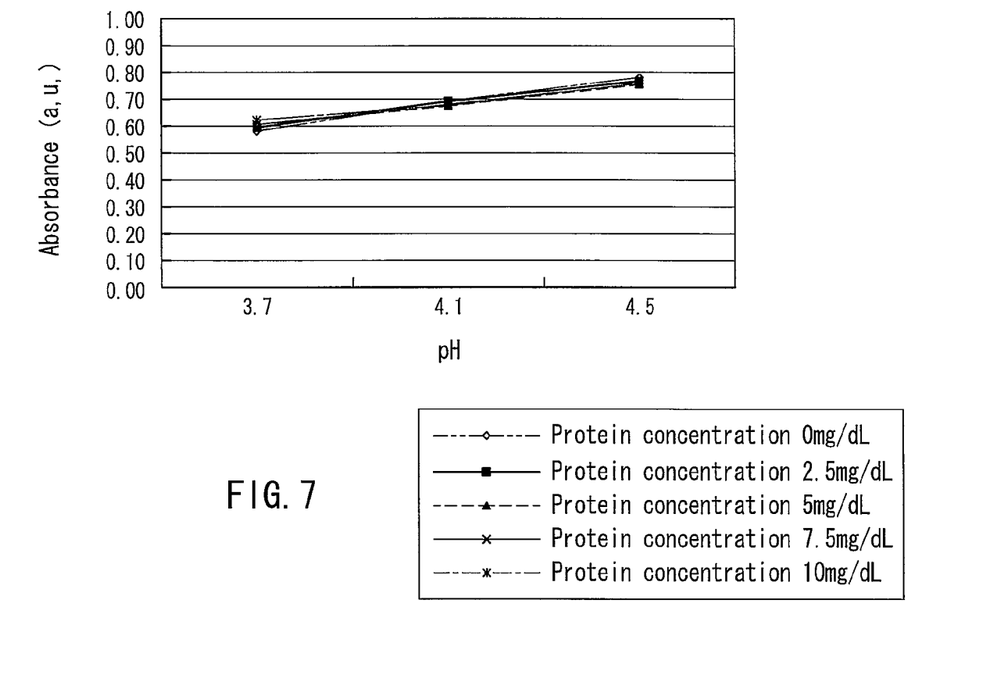
FIG. 7 is a graph showing exemplary results of pH measurements under various protein concentrations, the measurement having been performed with use of a pH indicating reagent that is not prone to being influenced by protein concentration in a solution.

BSA-added urine samples shown below were prepared by adding BSA to urine. Further, pH indicating reagent solutions shown below, as solutions of malic acid and ethyl orange, were prepared. The BSA-added urine samples and the pH indicating reagent solutions were mixed at a ratio of 1:1, whereby 15 types of mixed sample solutions were prepared, Absorbances (480 nm) of these mixed sample solutions were measured by a spectrophotometer (manufactured by JASCO Corporation). The results are shown in FIG. 7 and Table 11 below.

[BSA-Added Urine Sample Compositions]
   BSA (bovine serum albumin, manufactured by Sigma-Aldrich Co. LLC.) (0/5/10/15/20 mg/dL) was added to a urine sample

[pH Indicating Reagent Solution Compositions]
   0.2 M malic acid (pH 3.7/4.1/4.5)
   2.0 mg/dL ethyl orange (manufactured by Tokyo Chemical Industry Co., Ltd.)

TABLE 11

| | Absorbance | | | | |
|---|---|---|---|---|---|
| | 0 mg/dL | 2.5 mg/dL | 5 mg/dL | 7.5 mg/dL | 10 mg/dL |
| pH 3.7 | 0.58 | 0.59 | 0.61 | 0.61 | 0.62 |
| pH 4.1 | 0.69 | 0.69 | 0.87 | 0.68 | 0.68 |
| pH 4.5 | 0.78 | 0.77 | 0.75 | 0.76 | 0.76 |

As shown in FIG. 7 and Table 11 above, the absorbance of ethyl orange was not influenced by the protein concentration, and the absorbance varied with pH. Moreover, a pH value can be determined from an absorbance by a calculation formula of pH=(absorbance+0.15)/0.20, since an approximate curve is expressed as y=0.20x−0.15. Table 12 below shows pH calculated from absorbances shown in Table 11 by the calculation formula of pH=(absorbance+0.15)/0.20.

TABLE 12

| | Added protein concentration | | | | |
|---|---|---|---|---|---|
| | 0 mg/dL | 2.5 mg/dL | 5 mg/dL | 7.5 mg/dL | 10 mg/dL |
| pH 3.7 | 3.7 | 3.7 | 3.8 | 3.8 | 3.9 |
| pH 4.1 | 4.2 | 4.2 | 4.1 | 4.2 | 4.1 |
| pH 4.5 | 4.6 | 4.6 | 4.5 | 4.5 | 4.5 |

Assay with Use of pH Calculated from pH Indicating Reagent

Example 3

According to the data for the assay shown below that are based on both of absorbances of tetraburomophenol blue shown in Table 8 (Example 2 and Comparative Example 2) and pH calculated from the pH indicating reagent (Table 12), whether each mixed sample solution was positive or negative was determined as to the protein concentrations of the mixed sample solutions shown in Table 8. It should be noted that it was assumed that the positivity as an assay result means that the protein concentration is 10 mg/dL or more and that the negativity as an assay result means that the protein concentration is less than 10 mg/dL, as is the case with Example 2 and Comparative Example 2. The results are shown in Table 13 below.

The data for assay:
   at pH of 3M or below, a mixed sample solution is defined to need caution (acidic);
   at pH of 3.7, a mixed sample solution is defined to be negative when the absorbance is less than 0.53 and is defined to be positive when the absorbance is 0.53 or more;
   at pH of 3.8 or 3.9, a mixed sample solution is defined to be negative when the absorbance is less than 0.54, and is defined to be positive when the absorbance is 0.54 or more;
   at pH of 4.0 or 4.1, a mixed sample solution is defined to be negative when the absorbance is less than 0.55 and is defined to be positive when the absorbance is 0.55 or more;
   at pH of 4.2, a mixed sample solution is defined to be negative when the absorbance is less than 0.56 and is defined to be positive when the absorbance is 0.56 or more;
   at pH of 4.3, a mixed sample solution is defined to be negative when the absorbance is less than 0.57 and is defined to be positive when the absorbance is 0.57 or more;
   at pH of 4.4, a mixed sample solution is defined to be negative when the absorbance is less than 0.58 and is defined to be positive when the absorbance is 0.58 or more;
   at pH of 4.5, a mixed sample solution is defined to be negative when the absorbance is less than 0.59 and is defined to be positive when the absorbance is 0.59 or more; and
   at pH of 4.6 or below, a mixed sample solution is defined to need caution (alkaline).

TABLE 13

| | Added protein concentration | | | | |
|---|---|---|---|---|---|
| | 0 mg/dL | 2.5 mg/dL | 5 mg/dL | 7.5 mg/L | 10 mg/dL |
| | | Negative | | | Positive |
| pH 3.7 | Negative | Negative | Negative | Negative | Positive |
| pH 4.1 | Negative | Negative | Negative | Negative | Positive |
| pH 4.5 | Caution needed (alkaline) | Caution needed (alkaline) | Negative | Negative | Positive |

As shown in Table 13, it was possible to eliminate a false positive like that which occurred in Comparative Example 2, by performing the assay with use of pH values calculated from the pH indicating reagent. Additionally, since pH of a sample to be assayed was measured, a sample that changed to be extremely acidic or alkaline could be detected easily

INDUSTRIAL APPLICABILITY

The present disclosure is useful in, for example, fields of medicine, clinical assay, and the like.

EXPLANATION OF REFERENCE NUMERALS

1 Substrate
2 Reagent layer
3 Reagent layer
4 Reagent layer
10 Analysis tool

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A protein concentration assay method for assaying a concentration of protein in a sample, the method comprising:
    optically analyzing a color exhibited after the sample and a protein indicating reagent are brought into contact with each other in presence of a buffer to obtain an optically analyzed result;
    measuring pH of the sample using the same buffer as the buffer in which the protein indicating reagent and the sample are brought into contact;
    obtaining respective predetermined reference values corresponding to the measured pH of the sample;
    comparing the respective predetermined reference values and the optically analyzed result to obtain an assay result;
    outputting the assay result;
    wherein the color of the protein indicating reagent varies with pH and a concentration of protein.

2. The protein concentration assay method according to claim 1, wherein the protein indicating reagent is an octahalosulfophthalein-type dye, an octahalophenolphthalein-type dye, or a combination of these.

3. The protein concentration assay method according to claim 1, wherein the protein indicating reagent is selected from the group consisting of tetrabromophenol blue, tetrachlorophenol blue, 3',3",5,5"-tetraiode-3,4,5,6-tetrabromophenolsulfophthalein, 3,3"-diiode-5,5",3,4,5,6,-hexabromophenolsulfophthalein, and combinations of the same.

4. The protein concentration assay method according to claim 1, wherein a pH indicating reagent is used for measuring pH of the sample.

5. The protein concentration assay method according to claim 4, wherein the pH indicating reagent is ethyl orange.

6. The protein concentration assay method according to claim 1, wherein the predetermined reference values are recorded in association with pH values.

7. The protein concentration assay method according to claim 6, wherein the predetermined reference values include at least one selected from the group consisting of threshold value, threshold range, reference value, a coefficient for converting an optical analysis, data that define a formula for converting the optical analysis, and data that define a method for calibrating the optical analysis.

8. The protein concentration assay method according to claim 1, wherein the predetermined reference values include data that define a normal range for the measured pH.

9. The protein concentration assay method according to claim 1, wherein the sample is urine.

* * * * *